United States Patent [19]
Licchesi

[11] Patent Number: 6,069,693
[45] Date of Patent: May 30, 2000

[54] PROCESS FOR INSPECTING BONDING OF A LASER AMPLIFIER DISC

[75] Inventor: Victor Licchesi, Saint Etienne, France

[73] Assignee: Giat Industries, Versailles, France

[21] Appl. No.: 09/161,531

[22] Filed: Sep. 28, 1998

[30] Foreign Application Priority Data

Oct. 7, 1997 [FR] France .................................. 97 12467

[51] Int. Cl.[7] .................................................. G01N 21/00
[52] U.S. Cl. ........................ 356/237.1; 356/378; 356/382
[58] Field of Search ................................ 356/237.1, 382, 356/378

[56] References Cited

U.S. PATENT DOCUMENTS 4,849,036   7/1989   Powell et al. .

Primary Examiner—Frank G. Font
Assistant Examiner—Reginald A. Ratiff
Attorney, Agent, or Firm—Oliff & Berridge, PLC

[57] ABSTRACT

The invention relates to a laser amplifier disc comprising a neodymium-dope phosphate glass and a copper-doped phosphate glass cladding to entrap photons. The two glasses are bonded together using an adhesive film. The adhesive film is an epoxy resin. The invention also relates to a process inspecting the bonding of the laser amplifier disc cladding.

5 Claims, 3 Drawing Sheets

PROCESS FOR INSPECTING BONDING OF A LASER AMPLIFIER DISC

FIELD OF THE INVENTION

The invention relates to laser amplifier discs and a process cladding inspection for the discs.

DESCRIPTION OF THE RELATED ART

To obtain very high power lasers, such as, for example, one megajoule, a predetermined number of amplifier discs are arranged along the path of the beam to provide optical pumping. However, the phenomena of oscillation is known to occur, thereby reducing the gain provided by the laser amplifier. The phenomena of oscillation is linked to the production of a great number of photons emitted during amplification, the photons are stimulated at an angle greater than the critical angle of total reflection. The photons trapped between the faces of the amplifier discs reflect until the photons reach the edges of the discs edges. If the total loss from the edges of the discs is less than the gain, the oscillations will occur indefinitely. Another phenomenon to results from the photons being emitted in parallel to the disc surfaces, whereupon the photons reflect normally at the surface of the edges of the discs. Similarly, the phenomenon will occur indefinitely if the loss by reflection on the edges of the discs is less than the gain. Accordingly, cladding is used for the amplifier discs by arranging an inclined trap that allows the photons to pass beyond the discs without being able to return.

Laser amplifier discs are known that are obtained by hot duplicate moulding copper-doped phosphate glass along the periphery of each disc. However, duplicate moulding is difficult to implement and is very costly. Additionally, duplicate moulding also causes substantial stresses along the edge of each disc.

BRIEF SUMMARY OF THE INVENTION

The invention relates to an amplifier disc, and an inspection process for such a disc.

The invention includes a laser amplifier disc comprising a neodymium-doped phosphate glass with cladding having copper-doped phosphate glass to entrap photons. The assembly of the two glasses is obtained by using a film of adhesive having a thickness between 5 and 35 $\mu$m.

For example, the film of adhesive is a layer of epoxy resin having a thickness of between 20 and 30 $\mu$m, for example around 25 $\mu$m.

The process to inspect the bonding of a laser amplifier disc cladding, is characterised in that the process comprises the following steps:

forming a plate with parallel faces by arranging in the vicinity of the bonded cladding an identical cladding in an inverted position to obtain an incidence perpendicular to the direction of observation, lighting the adhesive film normally through the two layers of cladding, spotting the bonding defects of the two bonded glasses with the aide of a camera, and digitalizing the image obtained in shades of grey so as to spot the defects in the adhesive film and measure their size.

According to another step the process, the adhesive film is completely illuminated laterally.

The camera used is preferably of the CCD type, the illumination is accomplished using a halogen or fluorescent light source, and the normal illumination is transmitted via a ring of optical fibres arranged around the camera lens, whereas the lateral illumination is transmitted by optical Fibres arranged on either side of the adhesive film.

Thus, invention replaces the duplicate moulding process by bonding, which is easy to carry out and allows the possibility of reworking the manufacturing defects, thereby reducing the cost of the amplifier discs. Nevertheless, bonding requires fully controlled implementation processes in order to eliminate defects and cleaving that generate defects. This is why the bonding must be inspected as soon as each disc has been made and why an inspection process by image analysis has been adopted that enables the optical bonding defects between the cladding and the disc to be mapped out. An adhesive film has a surface area of around 800 mm×40 mm at the interface of the two glasses.

The process allows defects in the adhesive film to be detected and measured with a resolution of around 5 $\mu$m, allows them to be referenced and their position on the surface analyzed to be memorized, and allows the incidence of these defects with respect to the total surface area examined to be calculated.

BRIEF DESCRIPTION OF THE DRAWINGS

The above and other objects, characteristics, advantages and features of the invention will become apparent after reading the following description of the preferred embodiment taken in connection with accompanying the drawings in which.

DETAILED DESCRIPTION OF THE INVENTION

Figure 1:
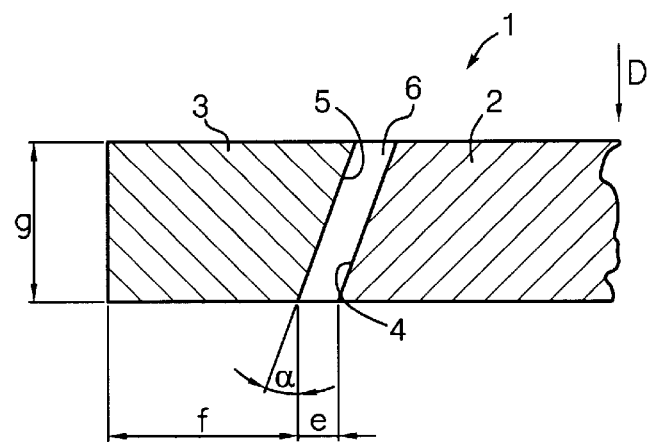
FIG. 1 is a partial sectional view of a disc according to the invention.

FIG. 1 is a partial sectional view of a laser amplifier disc 1 comprising a neodymium-doped phosphate glass disc 2 and copper-doped phosphate glass cladding 3. The respective adjacent faces 4 and 5 of disc 2 and cladding 3 have an angle $\alpha$ of approximately 1.6° degrees with respect to a direction D orthogonal to the surface of disc 2. This inclination angle $\alpha$ is necessary to improve the reduction of the amplification phenomena.

Faces 4 and 5 are bonded together using an adhesive film 6 of the epoxy resin type to make disc 2 and cladding 3 integral with one another. The adhesive film 6 is transparent to photons and has a continuous thickness e. The thickness e of the film is between 5 and 35 $\mu$m, more specifically between 20 and 30 $\mu$m, and advantageously around 25 $\mu$m.

The adhesion process itself is basic. The epoxy resin is evenly spread onto face 4 and/or face 5 to obtain a thickness e which is as even as possible and to facilitate bonding without bubbling. The image acquisition enables the quality of the bonding to be inspected.

By way of example, the cladding 3 and the disc 2 have a thickness g of approximately 40 mm and a length of approximately 800 mm.

Figure 2:
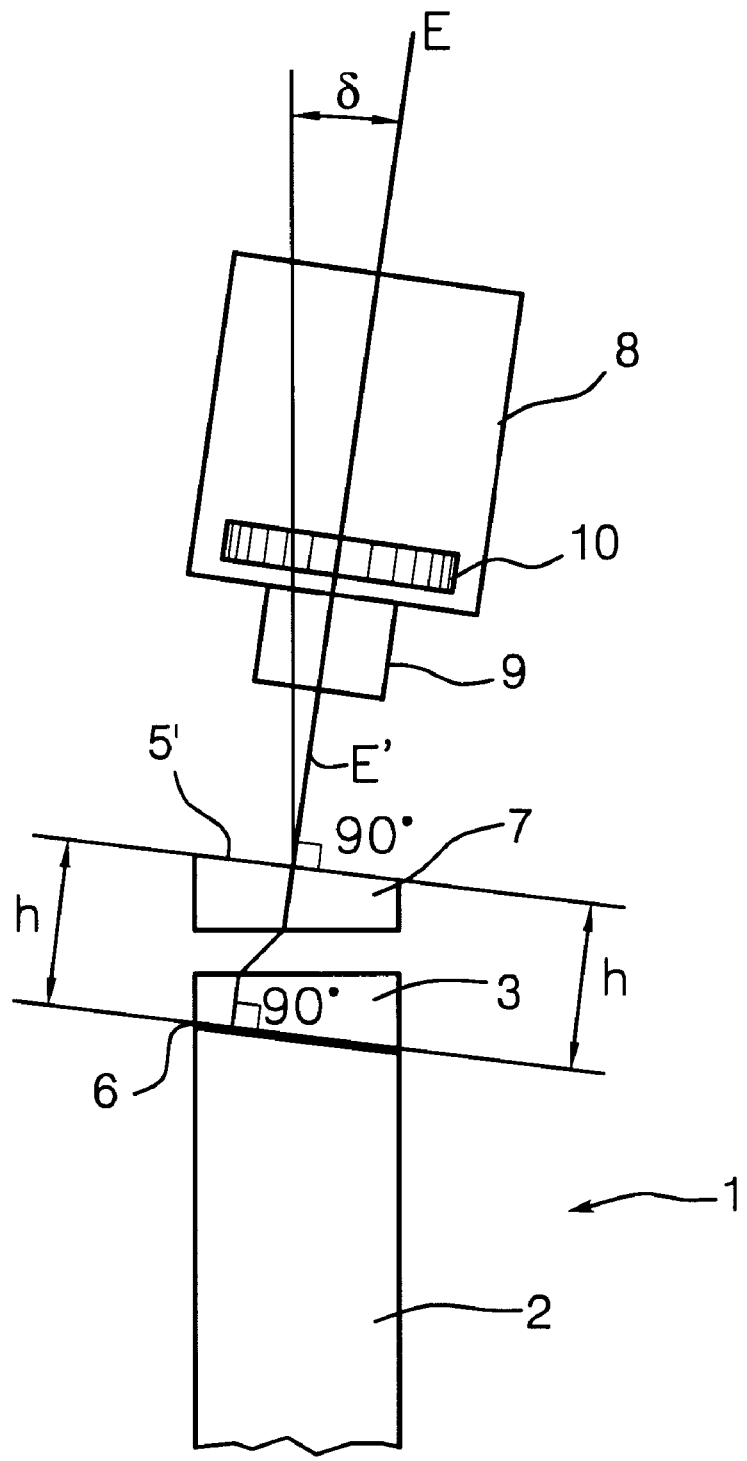
FIG. 2 is a schematic representation of the means to take up the shift linked to the inclination of the cladding to implement the process according to the invention;, FIG. 3 schematically represents the inspection installation to implement the process.

The performance of amplifier disc 1 is closely linked to the quality of the bonding. This is why another aspect of the invention lies in the inspection of the adhesive film 6 of, for example, epoxy resin. The angle α of the bonded faces 4 and 5 prevents constant focussing over the entire surface to be inspected. This problem is resolved by the process according to the invention illustrated in FIG. 2. To observe the adhesive film 6 at a constant incidence, a second cladding 7 is arranged along path E of the light beam. The second cladding 7 is similar to cladding 3 but with the faces inverted. In other words, the face 5' of the second cladding 7 corresponds to the face 5 of cladding 3 but is oriented towards the exterior. The second cladding 7 is placed at a distance of a few millimeters from cladding 3 compatible with the focussing of lens 9 of a camera 8. In fact, the assembly formed by the two claddings 3 and 7 forms a plate having parallel faces of thickness h. The camera 8 is fitted with a linear sensor 10 and is arranged so as to receive a light beam E' perpendicular to face 5' and to the adhesive film 6. As a result, camera 8 is offset from angle δ with respect to a vertical direction on which amplifier disc 1 is aligned. In this manner, the difference between the rays is nil, so that the definition is ensured at all points of linear sensor 10.

Figure 3:
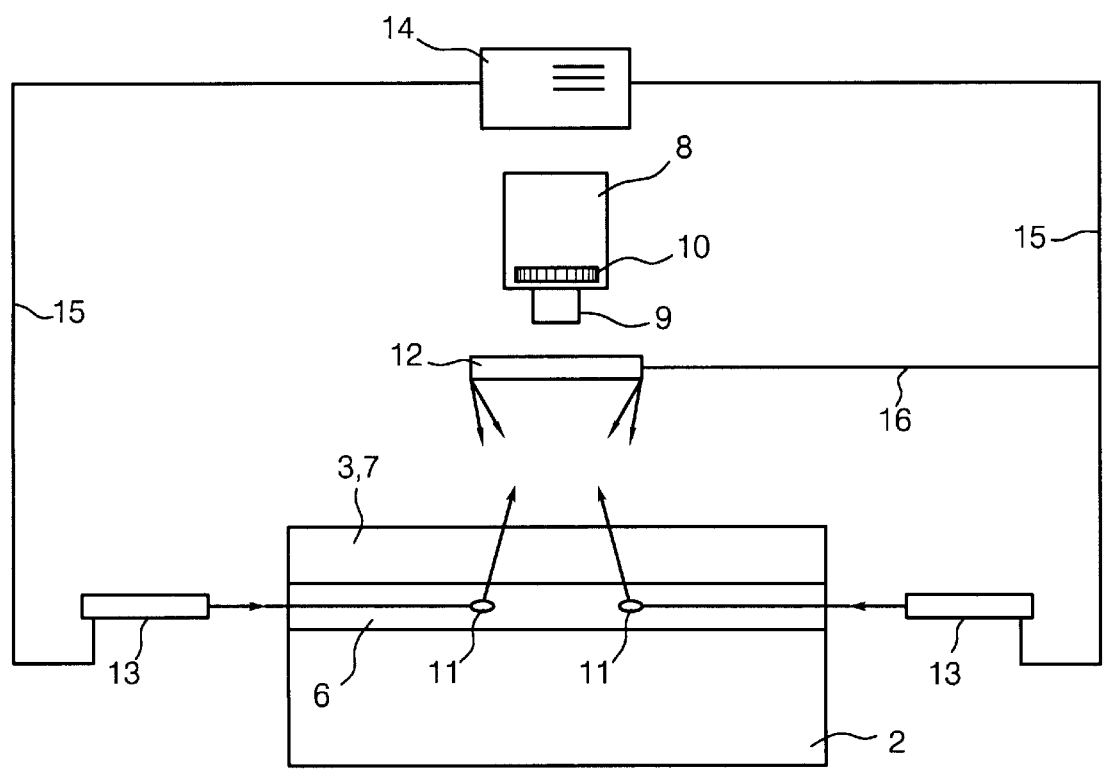

FIG. 3 schematically represents an installation enabling the bonding defects 11, for example scratches, air bubbles or dust, to be spotted on disc 2 fitted with its claddings 3 and 7. Camera 8 is arranged vertically with respect to disc 2 and adhesive film 6 is illuminated by a ring 12 of optical fibres arranged coaxially to lens 9 of camera 8. The adhesive film 6 can also be illuminated by optical fibres 13 arranged laterally with respect to adhesive film 6, the fibres being supplied by a halogen or fluorescent source 14 connected to conductors 15 and 16. Illumination can thereby be provided Perpendicularly and laterally to film 6.

Figure 4:
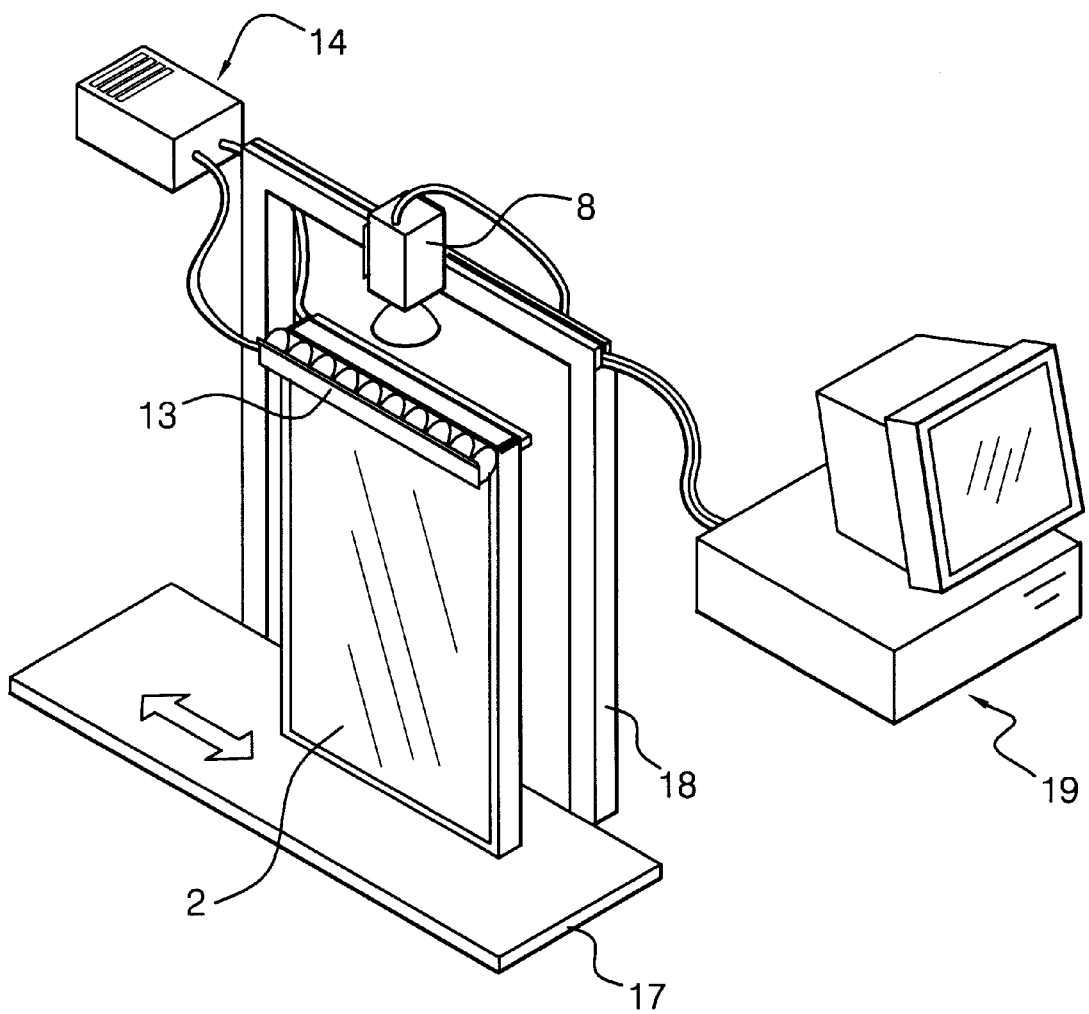
FIG. 4 is a schematic of the inspection station for the implementation of the process.

FIG. 4 represents a test bench for discs 2 which are brought by a system of linear displacement 17 in the vicinity of which a frame 18 is installed upon which camera 8 is fastened. The displacement system can, on the contrary, displace the camera with respect to the disc. In this case, the illumination can be amplified and can illuminate only the part seen by the camera. The amplifier disc 2 is here in the shape of a rectangular parallelepiped onto whose sides cladding 3 has been bonded by the adhesive film 6 which is illuminated by the optical fibre 13 assembly placed so as to illuminate through the adhesive film 6.

The images received by camera 8 are transmitted to a micro-processor 19 which processes the images according to an algorithmic sequence. The image is digitalized first in grey and then undergoes a thresholding operation, a hole filling operation and lastly a detection and measurement operation. Thresholding is a transformation which enables a phase of the image to be extracted by discriminating the shades of grey. The coded image is transformed through 256 shades of grey into a binary image. The hole filling operation ensures that all the pixels smaller than the defects detected are effectively counted during measurements by counting.

During detection, the defects highlighted by the illumination and revealed by the thresholding are recorded. The measurement operation enables the visualization and storage of all the measurements inherent to the defects after having calibrated the image by observation of a test pattern. The simplicity of the processing due to the quality of the acquisition enables processing time to be significantly reduced and thereby also inspection time.

By way of illustration, using a 410×480 pixel matrix CCD camera, the following results are obtained:

defects detected: 24 minimal surface: $2.87574 \times 10^2$ $\mu m^2$ maximal surface: $1.16611 \times 10^5$ $\mu m^2$ sum of the defective surfaces: $1.78200 \times 10^5$ $\mu m^2$ total surface analysed: $1.10428 \times 10^7$ $\mu m^2$ percentage of defects in the image: 1.61372%

Bonding of this type is acceptable from an industrial point of view Bonding must be carried out on the four sides of the cladded disc. The cartography, that is the number of defects per zone, will be compared with that specified for the acceptation or rejection of the discs 2.

I claim:

1. A process to inspect bonding of a laser amplifier disc cladding comprising the steps of:

forming a plate having parallel faces, said plate including a bonded first cladding;

arranging a second cladding near said first cladding, said second cladding being in an inverted position relative to said first cladding to obtain an incidence perpendicular to a direction of observation;

lighting an adhesive film through said first cladding and said second cladding in a direction normal relative to said parallel faces;

spotting bonding defects of two glasses bonded by the adhesive film with a camera; and digitalizing an image obtained by the camera in shades of grey so as to spot the bonding defects in the adhesive film and measure, a size of the defects.

2. The process according to claim 1, further comprising the step of:

laterally lighting the adhesive film completely through the adhesive film.

3. The process according to claim 2, wherein the lighting is accomplished using a CCD type camera.

4. The process according to claim 2, wherein the lateral lighting is accomplished using one of a halogen light source and a fluorescent light source.

5. The process according to claim 4, wherein the normal lighting is accomplished using a ring of optical fibres arranged around a lens of the camera and the lateral lighting is accomplished using optical fibres arrange on either side of the adhesive film such that lighting can be provided normally and laterally to the adhesive film.

* * * * *